United States Patent [19]
Lakshmanan

[11] Patent Number: 6,103,740
[45] Date of Patent: Aug. 15, 2000

[54] METHODS FOR LOWERING PLATELET COUNTS

[75] Inventor: Mark Chandrakant Lakshmanan, Zionsville, Ind.

[73] Assignee: Eli Lilly and Company, Indianapolis, Ind.

[21] Appl. No.: 09/129,324

[22] Filed: Aug. 4, 1998

Related U.S. Application Data

[60] Provisional application No. 60/056,203, Aug. 21, 1997.

[51] Int. Cl.[7] .................................................. A67K 31/445
[52] U.S. Cl. .......................... 514/324; 514/320; 514/408
[58] Field of Search .................................... 514/324, 320, 514/408

[56] References Cited

U.S. PATENT DOCUMENTS

| | | |
|---|---|---|
| 4,133,814 | 1/1979 | Jones et al. . |
| 4,380,635 | 4/1983 | Peters . |
| 4,418,068 | 11/1983 | Jones et al. . |
| 4,447,620 | 5/1984 | Sih et al. ................................ 548/336 |
| 4,847,276 | 7/1989 | Yarrington . |
| 5,075,321 | 12/1991 | Schreiber . |
| 5,391,557 | 2/1995 | Cullinan et al. . |
| 5,441,965 | 8/1995 | Sall et al. . |
| 5,445,941 | 8/1995 | Yang . |
| 5,476,862 | 12/1995 | Calnek et al. . |
| 5,482,949 | 1/1996 | Black et al. . |
| 5,508,292 | 4/1996 | Sall et al. . |

FOREIGN PATENT DOCUMENTS

| | | |
|---|---|---|
| 0 521 381 A1 | 6/1992 | European Pat. Off. . |
| 0 878 195 | 11/1998 | European Pat. Off. . |
| WO93/10113 | 5/1993 | Japan . |
| WO93/1074 | 6/1993 | WIPO . |
| WO 98/47365 | 4/1997 | WIPO . |

OTHER PUBLICATIONS

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.
Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.
Bryant et al., "Raloxifene is a Tissue Specific Estrogen Agonist", Am Soc. Bone & Min. Res., Tampa, Sep. 18–22, 1993.
Frolick et al., "In Vivo and In Vitro Metabolism of Raloxifene", Am. Soc. Bone & Min. Res., Tampa, Sep. 18–22, 1993.
Glasebrook et al., "Multiple Binding Sites for the Anti–estrogen Raloxifene", Am Soc. Bone & Min. Res., Tampa, Sep. 18–22, 1993.
Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.
Sato et al., "DEXA Analysis of Raloxifene Effects on the Bones From Ovariectomized Rats", Am. Soc. for Bone and Min. Res., Tampa, Sep. 18–22, 1993.
Yang et al., "Raloxifene an Anti–Estrogen, Simulates the Effects of Estrogen in Inhibiting Bone Resorption Through Regulating TGFB–3 Expression in Bone;".Am Soc. for Bone and Min. Res., Tampa, Sep. 18–22, 1993.
Black et al., "Distinct, Structure–Related Profiles of Estrogenic and Anti–Estrogenic Activity in the Tamoxifen and LY117018 Series;" The Endocrine Society, Abstract 1982.
Black et al., "Uterine Bioassay of Tamoxifen, Trioxifene, and New Estrogen Antagonist (LY117018) in Rats and Mice," Life Sciences, 26:1980, 1453–1458.
Black et al., "Differential Interaction of Antiestrogens with Cytosol Estrogen Receptors," Molecular and Cellular Endocrinology, 22:1981, 95–103.
Black et al., "Evidence for Biological Action of the Antiestrogens LY117018 and Tamoxifen by Different Mechanisms," Endocrinology 109;1981, 987–989.
Black, L.J. "Biological Actions and Binding Properites of a New Estrogen Antagosist LY117018," In: Homone Antagonists, 129–82, 1982 (M.K. Agarwal ed.) Walter de Gruyter and Co., Berlin New York.
Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.
Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.
Black et al., Antagonism of Estrogen Action with a New benzothiophene Derived Antiestrogen, Life Sciences, 32:1983. 1031–1036.

(List continued on next page.)

*Primary Examiner*—Zohreh Fay
*Attorney, Agent, or Firm*—William R. Boudreaux; James J. Sales

[57] ABSTRACT

A method of safely lowering platelet count in a human which comprises the administration to a human in need thereof of an effective amount of a compound of formula I

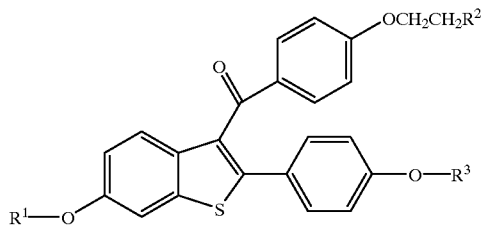

wherein $R^1$ and $R^3$ are, independently, —H, —$CH_3$, —CO($C_1$–$C_6$ alkyl), or —COAr, where Ar is optionally substituted phenyl;

$R^2$ is selected from the group consisting of pyrrolidine, piperidine, and hexamethyleneimino; or a pharmaceutically acceptable salt or solvate thereof.

4 Claims, No Drawings

OTHER PUBLICATIONS

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl)ethoxyl]–phenyl] methanone, methanesulfonic acid salt, Journal of Medicinal Chemistry 22;1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl][4–[2–91–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

Dina M. Bitar et al., Suppression of Experimental Autoimmune Encephalomyelitis by the Oral Administration of Myelin Basic Protein, Cellular Immunology 112, 364–370, 1988.

Paul J. Higgins, et al., Suppression of Experimental Autoimmune Encephalomyelitis by Oral Administration of Myelin Basic Protein and its Fragments, The Journal of Immunology, vol. 140(2), 440–445, Jan. 15, 1988.

Oral Tolerance to Myelin Basic Protein and Natural Recovery from Experimental Autoimmune Encephalomyelitis Are Associated with Downregulation of Inflammatory Cytokines and Differential Upregultion of Transforming Growth Factor β, Intererleukin 4, and Prostaglandin E Expression In the Brain, J. Exp. Med., vol., 176, 1355–1364, Nov. 1992.

C. D. Jones, et al. Antiestrogens. 2. Structure–Activity Studies in a Series of 3–Aroyl–2–arylbenzo{b}thiophene Derivatives Leading to{6–Hyddroxy–2–(4–hydroxyphenyl)benzo{b}thien–3–yl] [4–[2–(1–piperidinyl)ethoxy]–phenyl]methanone Hydrochloride (LY156758), A remarkably Effective Estrogen Antagonist With Only Minimal Intrinsic Estrogenicity, J. Med. Chem., 1984, 27, 1057–1066.

A Hendrick, et al., Tamoxifen and Thromboembolism, Journal of the American Medical Association, vol. 243, No. 6, Feb. 8, 1980.

Radwanska, E., The Role of Reproductive Hormones in Vascular Diseases and Hypertension, Steroids, 58(12), 605, Dec. 1993.

Pfilger, et al., Acta Med. Austriaca, 18(3), 68–72, 1991.

Database HCAPLUS on STN, AN 1988:32668, "Evidence that transforming growth factor–beta is a hormonally regulated negative growth factor in human breast cancer cells". Cell, (Cambridge, Mass.) 1987, 48(3), 417–428.

METHODS FOR LOWERING PLATELET COUNTS

This Application claims the benefit of U.S. Provisional Application Ser. No. 60/056,203, filed Aug. 21, 1997.

FIELD OF THE INVENTION

The current invention provides methods for lowering platelet counts in humans, particularly post-menopausal women.

BACKGROUND OF THE INVENTION

Platelets are a major cell type found in the blood and are critical to maintaining normal hemostasis. Platelets are derived from marrow stem cells and are usually found either in the circulation or sequestered in the spleen. A normal number of platelets in human blood is around 150,000 to 400,000 per mL, the condition in which the number of platelets falls substantially below this level is referred to as a thrombocytopenic state, conversely an overabundance of platelets is referred to as a condition of thrombcytosis or thrombocythemia.

A major function of the platelet is to control bleeding and to plug any due to rupture of the vasculature via clot formation. The platelet functions not only as an integral and structural element of a clot, but also is responsive to the surrounding conditions and reacts by releasing a wide variety of mediators which effect surrounding cells and tissues. Upon encountering a aberrant situation, e.g., exposed collagen or basement membrane, platelets adhere, aggregate, and release granules containing mediators, such as ADP, smooth muscle mitogens, prostaglandins, thromboxanes, catecholamines, clotting factors, and the like. These mediators not only promote further platelet aggregation and clot formation, but also effect the behavior of smooth muscle cells causing constriction and proliferation. Additionally, these mediators effect other circulating cells, such as lymphocytes and inflammatory cells, which may initiate biological sequelae quite different from clot formation. Many of these other sequelae often have pathological consequence.

It is essential for hemostasis that an adequate number of platelets are available for the clotting reaction. Failure of the clotting system is usually considered a very serious and life-threatening condition. In cases, where the number of platelets drops below 100,000 per mL, there is cause for concern and may result in therapeutic intervention. Platelet counts less than 40,000 are on the threshold of spontaneous bleeding and must be aggressively treated, usually with platelet infusions. Such drops in platelet count may occur in cancer patients treated with cytotoxic agents or radiation, in trauma patients especially burn injuries, or in patients with immune abnormalities. (For further information, e.g., see: "Harrison's Principles of Internal Medicine", Eds. Isselbacher, K. J., et al., 9th Ed., McGraw-Hill Book Co., NYC, 1980, Chap. 54, pp. 273–276, Chap. 361, pp. 1555–1557, and references cited therein.)

However, paradoxically, as important and necessary as platelets are, they can often contribute to many detrimental conditions. For example, they are participatory and perhaps causative elements in inappropriate thrombotic events such as occlusion of arteries and vessels which precipitate ischemic events and tissue damage. Inappropriate activation of platelets can be life-threatening and there are many medical conditions which increase the risk of such activations, such as patients suffering from atherosclerosis, patients recovering surgery or trauma, patients recovering from angioplasty, and the like. One envisioned method of lowering the risk of such inappropriate activations is to lower the total number of normal platelets in the circulation. In a recent clinical report, it was shown that there was a direct correlation between platelet count and function and fatal coronary heart disease, i.e., patients with the highest platelet count and aggregability were most likely to succumb. Thus, it would seem reasonable that an agent which reduces the platelet count should demonstrate a beneficial effect in preventing coronary disease. (See: "Blood Platelet Count and Function Are Related to Total and Cardiovascular Death in Apparently Healthy Men", Thaulow, E., et al., Circulation, 84(2), pp.631–617, 1991 and "Thrombocytes and Coronary Heart Disease", Wilhelmsen, L., Circulation, 84(2), pp. 936–937., 1991).

Although a beneficial effect seems reasonable with a reduction of platelet count, it is critical that reduction does not produce thrombocytopenia. An ideal agent would have to reduce the platelet count without compromising appropriate clotting activity, i.e., the platelet count would need to remain in the normal range.

Recently, a clinical study was reported which demonstrated a lowering of the platelet count in women taking the compound tamoxifen. However, tamoxifen is known to have substantial estrogen-agonist properties, especially in the uterus, and would thus be a less than ideal agent. (See: "Effect of Tamoxifen on Measurements of Hemostasis in Healthy Women", Mannucci, P. M., et al., Arch. Internal Med., 156, Sep. 9, 1996. pp. 1806–1810.)

SUMMARY OF THE INVENTION

The current invention provides methods for lowering the platelet count in a human, which comprises the administration to a human in need thereof an effective amount of a compound of formula I.

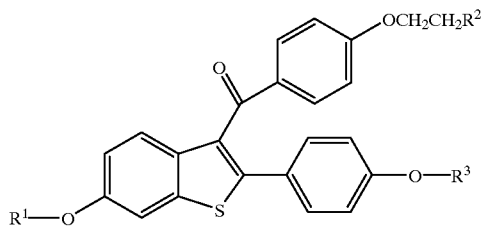

wherein $R^1$ and $R^3$ are, independently, —H , —$CH_3$, —CO($C_1$–$C_6$ alkyl), or —COAr, where Ar is optionally substituted phenyl;

$R^2$ is selected from the group consisting of pyrrolidine, piperidine, and hexamethyleneimino; or a pharmaceutically acceptable salt or solvate, thereof.

DETAILED DESCRIPTION OF THE INVENTION

The current invention is related to the discovery that a select group of 2-aryl benzo[b]thiophenes (the compounds of formula I) are useful for lowering platelet count.

General terms used in the description of compounds herein described bear their usual meanings. For example, "$C_1$–$C_6$ alkyl" refers to straight or branched aliphatic chains of 1 to 6 carbon atoms including methyl, ethyl, propyl, iso-propyl, n-butyl, pentyl, hexyl and the like.

The term "substituted phenyl" refers to a phenyl group alone or having one or more substituents selected from the group consisting of $C_1$–$C_4$ alkyl, $C_1$–$C_4$ alkoxy, hydroxy, nitro, chloro, fluoro, or tri(chloro or fluoro)methyl. "$OC_1$–$C_4$ alkyl" refers a $C_1$–$C_4$ alkyl group attached through an oxygen bridge such as, methoxy, ethoxy, n-propoxy, iso-propoxy, and the like.

The term "pharmaceutically acceptable salt" refers to either acid or base addition salts which are known to be non-toxic and are commonly used in the pharmaceutical literature. Commonly used acid addition salts are inorganic salts formed by the addition of sulfuric acid, nitric acid, hydrochloric acid, hydrobromic acid phosphoric acid, phosphorous acid and the like; or organic salts formed by the addition of acetic acid, formic acid, benzoic acid, citric acid, methanesulfonic acid and the like. Commonly used basic addition salts are the salts formed by alkali or alkaline earth hydroxides, ammonium hydroxide, alkyl or aromatic amines and the like. A preferred salt of this invention is the hydrochloride salt.

The term "solvate" refers to a molecular complex of a compound of formula I with one or more solvent molecules. Such solvent molecules would be those commonly used in the pharmaceutical literature, which are known to be innocuous to the recipient, e.g., water, ethanol, and the like.

The compounds of this invention are derivatives of centrally located carbon, i.e., the "—CO—" moiety in formula I, thus derivatives are methanones, e.g., a compound of A—CO—B, would be named [A][B]methanone. Further the compounds of formula I are derivatives of benzo[b]thiophene which is named and numbered according to the Ring Index, The American Chemical Society, as follows:

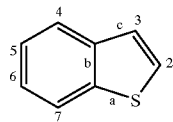

Thus, raloxifene hydrochloride, which is a preferred embodiment of this invention, is a compound of formula I, where $R^1$ and $R^3$ are both hydrogen and $R^2$ is a piperidinyl ring, the hydrochloride salt thereof. Raloxifene hydrochloride is named [2-(4-hydroxyphenyl)-6-hydroxybenzo[b]thie-3-yl][4-[2-(1-piperidenyl) ethoxy]phenyl] methanone hydrochloride.

All of the compounds used in the methods and formulations of the current invention can be made according to procedures, such as those detailed in U.S. Pat. No. 4,133,814 and U.S. Pat. No. 4,418,068, each of which is included by reference, herein. In general, the process starts with a benzo[b]thiophene having a 6-hydroxyl group and a 2-(4-hydroxylphenyl) group. The starting compound is protected, alkylated, and de-protected to form the compounds of formula I. The formula I compounds which are carboxylic esters may be prepared by methods described in U.S. Pat. No. 5,393,763, which included by reference, herein.

The compounds of formula I are members of a group of compounds previously known as antiestrogens, but which have selective estrogenic agonist and antagonist pharmacologic activities. For example, formula I compounds act as estrogen agonists in treating pathologic sequelae caused by the cessation of menses in females (see: Draper et al., "Effects of Raloxifene (LY139481 HCl) on Biochemical Markers of Bone and Lipid Metabolism in Healthy Postmenopausal Women", Hong Kong, Fourth Int'l. Symp. on Osteoporosis, Mar. 29, 1993.; U.S. Pat. Nos. 5,393,763, 5,464,845, and 5,391,557). In addition, the compounds of formula I have been shown to inhibit angiogensis, see: U.S. Pat. No. 5,610,166, which is incorporated herein by reference.

As used herein, the term "effective amount" means an amount of compound of the present invention which is capable of safely lowering platelet count in a human, and preferably a post-menopausal woman.

As used in the methods of the current invention, the term "lowering platelet count", means a reduction in the number of circulating platelets without reaching a level of thrombocytopenia (<100,000 per mL) which would have the potential of precipitating serious bleeding events.

By "pharmaceutically acceptable formulation" it is meant that the carrier, diluent, solvent, excipients and salt must be compatible with the active ingredient (a compound of formula I) of the formulation, and not be deleterious to the recipient thereof.

Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonire; and lubricants such as talc, calcium and magnesium stearate and solid polyethyl glycols. Final pharmaceutical forms may be pills, tablets, powders, lozenges, syrups, aerosols, saches, cachets, elixirs, suspensions, emulsions, ointments, suppositories, sterile injectable solutions, or sterile packaged powders, depending on the type of excipient used.

The particular dosage of a compound of formula I required to safely lower platelet count according to this invention will depend upon the particular symptom and severity. Such considerations as a dosage, route of administration, and frequency of dosing are best decided by the attending physician. Generally, accepted and effective doses for oral or parenteral administration will be from 10 mg to 800 mg, and more typically between 20 mg and 100 mg. A particularly preferred dose is 60 mg/day via the oral route, especially in a post-menopausal female. Such dosages will be administered to a patient in need of treatment from once to three times each day or as often as needed to effectively and safely lower platelet count.

The formulations which follow are given for purposes of illustration and are not intended to be limiting in any way. The total active ingredients in such formulations comprises from 0.1% to 99.9% by weight of the formulation. The term, "active ingredient" means a compound of formula I, preferably Raloxifene hydrochloride.

| Formulation 1: Gelatin Capsules | |
|---|---|
| Ingredient | Quantity (mg/capsule) |
| Active Ingredient | 50–600 |
| Starch NF | 0–500 |
| Starch flowable powder | 0–500 |
| Silicone fluid 350 centistrokes | 0–15 |

The ingredients are blended, passed through a No. 45 mesh U.S. sieve, and filled into hard gelatin capsules.

| Formulation 2: Tablets | |
|---|---|
| Ingredient | Quantity (mg/tablet) |
| Active Ingredient | 50–600 |
| Starch | 10–50 |
| Cellulose, microcrystalline | 10–20 |
| Polyvinylpyrrolidone (as 10% solution in water) | 5 |
| Sodium carboxymethyl cellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50–60° C. and passed through a No. 18 mesh U.S. sieve. The sodium carboxymethyl cellulose, magnesium stearate, and talc, previously passed through a No. 60 mesh U.S. sieve, are added to the above granules and thoroughly mixed. The resultant material is compressed in a tablet forming machine to yield the tablets.

| Formulation 3: Aerosol | |
|---|---|
| Ingredient | Weight % |
| Active Ingredient | 0.50 |
| Ethanol | 29.50 |
| Propellant 22 (Chlorodifluoromethane) | 70.00 |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

| Formulation 4: Suspension Suspensions each containing 100 mg of a compound of formula I per 5 mL dose. | |
|---|---|
| Ingredient | Weight |
| Active Ingredient | 100 mg |
| Sodium carboxymethyl cellulose | 50 mg |
| Syrup | 1.25 mL |
| Benzoic acid solution (0.1M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the entire mixture to the required volume.

ASSAY 2,043 healthy, post-menopausal women were selected. These patients were randomized between a control group having 584 patients, and the following three test groups: Raloxifene HCL 30 mg/dy—288 patients; raloxifene HCL 60 mg/dy—584 patients; Raloxifene HCY 120 or 150 mg/dy—590 patients. Patients in the control group received a daily oral placebo. The duration of the clinical trial was two years. As a portion of the patient's overall evaluation, various clinical tests and parameters were measured at intervals. Among the periodic parameters measured was platelet count.

Comparison of the initial platelet count with the endpoint values demonstrated a decrease of 7–9% in circulating platelets in the test group patients, as compared to the control group. No episodes of unusual bleeding were experienced during the study and platelet counts never dropped below 100,000 per mL.

We claim:

1. A method for lowering platelet count in a human which comprises the administration to a human in need thereof an effective amount of a compound of formula I

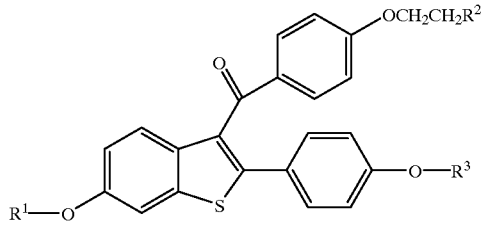

wherein $R^1$ and $R^3$ are, independently, —H , —CH$_3$, —CO ($C_1$–$C_6$ alkyl), or —COAr, where Ar is optionally substituted phenyl;

$R^2$ is selected from the group consisting of pyrrolidine, piperidine, and hexamethyleneimino; or a pharmaceutically acceptable salt or solvate thereof.

2. A method according to claim 1 wherein said compound is [2-(4-hydroxyphenyl)-6-hydroxybenzo[b]thien-3-yl][4-[2-(1-piperidinyl)ethoxy]phenyl]methanone hydrochloride.

3. A method of claim 1 wherein said human is a post-menopausal women.

4. A method according to claim 3 wherein compound is administered in an amount of 60 mg/day via the oral route.

* * * * *